(12) United States Patent
Kyöstilä

(10) Patent No.: US 9,241,680 B2
(45) Date of Patent: Jan. 26, 2016

(54) DENTAL CARE APPARATUS

(75) Inventor: Heikki Kyöstilä, Helsinki (FI)

(73) Assignee: PLANMECA OY, Helsinki (FI)

( * ) Notice: Subject to any disclaimer, the term of this patent is extended or adjusted under 35 U.S.C. 154(b) by 913 days.

(21) Appl. No.: 13/000,659

(22) PCT Filed: Jun. 25, 2009

(86) PCT No.: PCT/FI2009/050568
§ 371 (c)(1),
(2), (4) Date: Dec. 22, 2010

(87) PCT Pub. No.: WO2009/156591
PCT Pub. Date: Dec. 30, 2009

(65) Prior Publication Data
US 2011/0104634 A1 May 5, 2011

(30) Foreign Application Priority Data
Jun. 27, 2008 (FI) ...................... 20080417

(51) Int. Cl.
| A61B 6/14 | (2006.01) |
| A61B 6/04 | (2006.01) |
| A61G 15/14 | (2006.01) |
| A61G 15/16 | (2006.01) |

(52) U.S. Cl.
CPC ... *A61B 6/14* (2013.01); *A61B 6/04* (2013.01); *A61B 6/0478* (2013.01); *A61G 15/14* (2013.01); *A61G 15/16* (2013.01)

(58) Field of Classification Search
CPC ........................................ A61B 6/14
USPC .................. 378/10, 38, 39, 40, 196, 197, 209
See application file for complete search history.

(56) References Cited

U.S. PATENT DOCUMENTS

| 3,922,788 A * | 12/1975 | Rota ...................... A61G 15/14 |
| | | 312/209 |
| 4,221,970 A | 9/1980 | Ciavattoni |
| 4,249,900 A | 2/1981 | Hoelzer et al. |
| 4,934,933 A | 6/1990 | Fuchs |

(Continued)

FOREIGN PATENT DOCUMENTS

| DE | 29520999 | 10/1996 |
| EP | 1 457 155 | 9/2004 |

(Continued)

*Primary Examiner* — Allen C. Ho
(74) *Attorney, Agent, or Firm* — Fay Sharpe LLP

(57) ABSTRACT

The invention relates to a dental care apparatus which comprises a dental care unit (4) and a patient chair (5) arranged in the immediate vicinity of each other and to which is structurally connected at least a treatment arm (7) for dental care instruments (9) and/or an arm for holding some other appliance or device used in a dental environment, such as a display (3), and which additionally comprises at least one arm part (11) arranged in the immediate vicinity of the dental care unit (4) whereon at least either of the imaging means an X-radiation source (14) and an image information receiver (15) is arranged, in which apparatus (2) the mutual position of said arm part (11) and patient chair (5) is arranged such that the arm part (11) is located or is positionable substantially above said patient chair (5), and in which apparatus said arm part (11) carrying at least one imaging means (14, 15) and/or the patient chair (5) is arranged rotatable by an actuator.

17 Claims, 5 Drawing Sheets

(56) References Cited

U.S. PATENT DOCUMENTS

Figure 1:
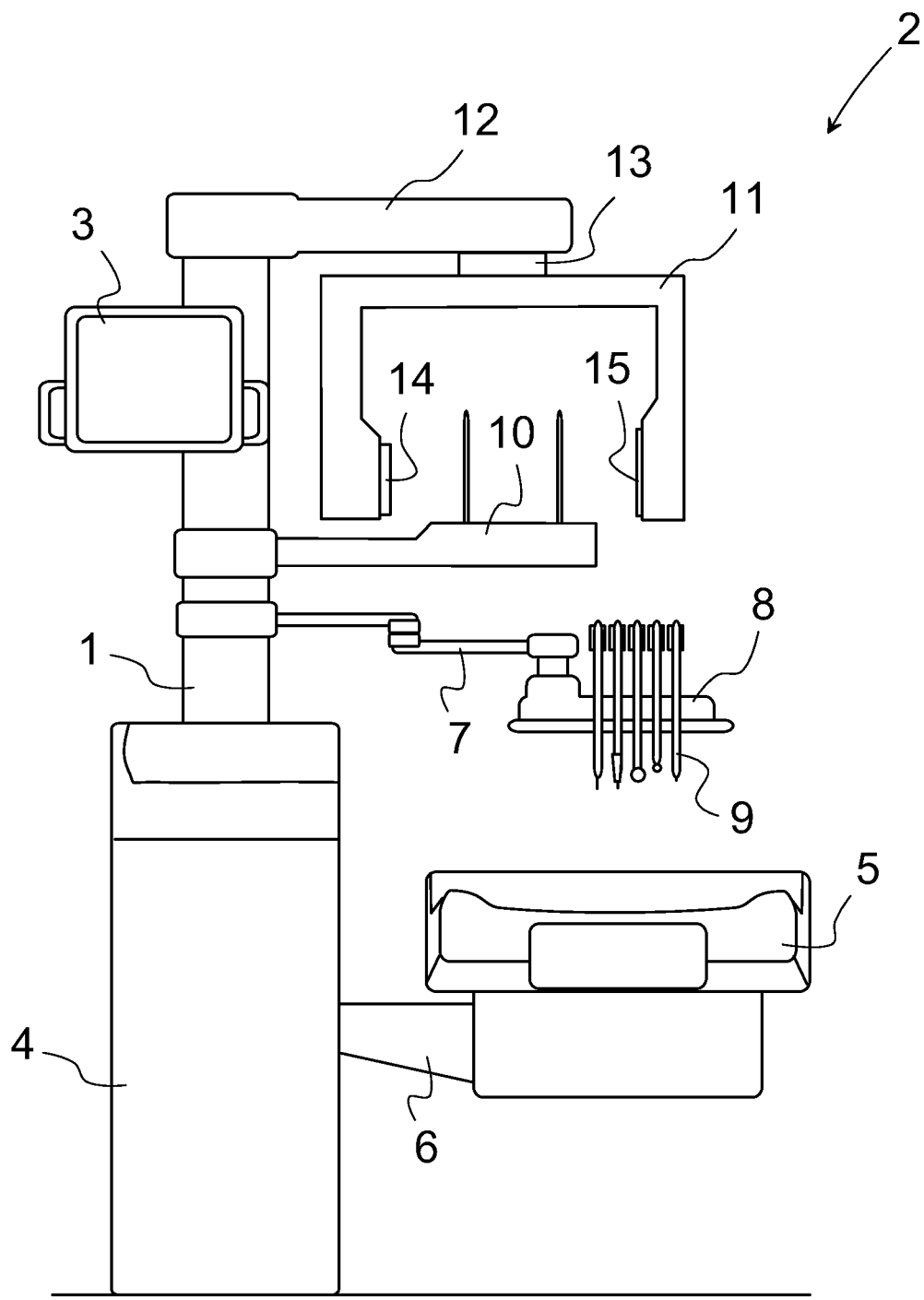

| | | | | |
|---|---|---|---|---|
| 5,642,392 A * | 6/1997 | Nakano et al. | | 378/38 |
| 6,148,058 A * | 11/2000 | Dobbs | | 378/19 |
| 6,466,641 B1 * | 10/2002 | Virta et al. | | 378/38 |
| 6,496,558 B2 * | 12/2002 | Graumann | | 378/39 |
| 6,619,839 B2 * | 9/2003 | Yoshimura | | 378/38 |
| 6,638,068 B2 * | 10/2003 | Lingenhole et al. | | 433/114 |
| 7,011,519 B2 * | 3/2006 | Castellini | | 433/79 |
| 7,048,237 B2 * | 5/2006 | Hubner | | F16M 11/08 248/121 |
| 7,048,439 B2 * | 5/2006 | Hubner | | A61B 6/105 248/288.51 |
| 7,187,749 B2 * | 3/2007 | Suzuki | | A61B 6/0478 378/162 |
| 7,195,219 B2 * | 3/2007 | Irwin et al. | | 433/79 |
| 7,197,107 B2 * | 3/2007 | Arai et al. | | 378/20 |
| 7,347,622 B2 * | 3/2008 | Sadakane et al. | | 378/197 |
| 7,421,059 B2 * | 9/2008 | Suzuki | | A61B 6/04 378/38 |
| 7,486,767 B2 * | 2/2009 | Sonobe et al. | | 378/39 |
| 7,515,683 B2 * | 4/2009 | Nanni et al. | | 378/38 |
| 7,545,913 B2 * | 6/2009 | Connelly | | A61B 6/14 378/162 |
| 7,577,232 B2 * | 8/2009 | Tachibana | | G03B 42/026 378/116 |
| 7,773,720 B2 * | 8/2010 | Honjo | | A61B 6/032 378/189 |
| 7,787,586 B2 * | 8/2010 | Yoshimura | | A61B 6/032 378/38 |
| 7,945,016 B2 * | 5/2011 | Bothorel et al. | | 378/38 |
| 8,300,762 B2 * | 10/2012 | Suzuki et al. | | 378/39 |
| 8,503,603 B2 * | 8/2013 | Tancredi et al. | | 378/39 |
| 2005/0053199 A1 | 3/2005 | Miles | | |
| 2006/0046226 A1 | 3/2006 | Bergler et al. | | |

FOREIGN PATENT DOCUMENTS

| | | |
|---|---|---|
| EP | 1 790 291 | 5/2007 |
| FI | 79459 | 1/1990 |
| WO | WO 2008/035828 | 3/2008 |

* cited by examiner

DENTAL CARE APPARATUS

The present invention relates to a dental care apparatus, which comprises a dental care unit and a patient chair arranged in the immediate vicinity of each other, and to which is structurally connected a treatment arm for dental care instruments and/or an arm for some other appliance or device used in dental environment, such as a display.

In prior art, dental care apparatuses have been implemented as different constructions i.a. for different dentist cultures. The dental care unit itself is a device used in connection with dental treatment, an essential and traditional function of which is to supply to the dental care instruments used by the dentist the physical magnitudes required for their operation, such as electricity, compressed air and/or water. On the other hand, dental treatment also involves use of means for sucking blood, saliva and pieces of tartar out of a patient's mouth.

Many dental clinics have also acquired X-ray devices specifically designed to be used in connection with diagnosing related to dental treatment. Typical devices of this category are an intraoral X-ray device, which is used to take images by positioning a film, a sensor or equivalent in the patient's mouth for the imaging, and e.g. a panoramic imaging device and a combined panoramic/skull imaging device designed for extraoral imaging, out of which at least the more advanced ones can be used, inter alia, for taking various layer images (tomograms) of anatomies of the skull area. A panoramic X-ray device is used e.g. for imaging of the set of teeth, bones and joints of the jaw as well as the oral and maxillary sinuses of a patient being examined. Also, 3D X-ray imaging is nowadays applied in connection with dental radiography as well.

To keep instruments at hand, the dental care unit is typically provided with various holders and/or arms. On the other hand, even several different arms may be connected to a dental care unit, such as an arm for an operating light and nowadays e.g. for a display. In some constructions, a mechanism for raising the patient chair, and possibly its control system as well, is arranged in connection with the dental care unit.

A prior-art practice includes disposing intraoral X-ray devices in the dental treatment space in the vicinity of a dental care unit, whereas the considerably more massive extraoral X-ray device requiring more space is typically disposed in a separate imaging room or space, which may be located even a long way from the actual dental treatment space. It is even possible that the clinic has no X-ray device at all. In view of a smooth dental care process, it is naturally awkward if the treatment work or process has to be interrupted because of the patient needing to drop in to get imaged. Furthermore, in addition to the space requirement, an extraoral X-ray device in itself always also requires a user interface, connections for transmission of resources and information, as well as other accessories that may be needed, of its own.

The object of the present invention and its preferable embodiments is to provide new solutions in view of the above-described prior art problems in the form of a dental care apparatus that can be used for both ordinary dental work and for dental extraoral X-ray imaging. The object of the different embodiments of the invention is to provide an apparatus that allows dental extraoral X-ray images to be taken of the patient without a need for the patient to leave the patient chair during the dental treatment session. On the other hand, some of the embodiments of the invention aim at providing a dental treatment space arrangement wherein the same X-ray imaging resources have been arranged to be utilized in connection with at least two dental care units disposed in the treatment space. The invention is characterized by what is disclosed in the characterizing part of claim 1 presented below. The attached dependent claims set forth a few preferred embodiments of the invention.

The invention with its different embodiments provides possibilities for saving space at a dental clinic. The various embodiments of the invention also make it possible to take many kinds of X-ray images in a flexible manner in connection with an ordinary dental treatment session, obviating the need to make a separate appointment for X-ray imaging. Further, various embodiments of the invention allow the same resources to be utilized in the dental care unit and in the X-ray imaging equipment. In the preferred embodiments of the invention, the structure supporting the imaging means can be implemented in a lighter and simpler form than in many prior-art extraoral X-ray imaging devices by omitting from the construction the means for adjusting the height position of the imaging station, while this adjustment can be performed by using the height adjustment structures of the patient chair comprised in the apparatus.

Figure 3:
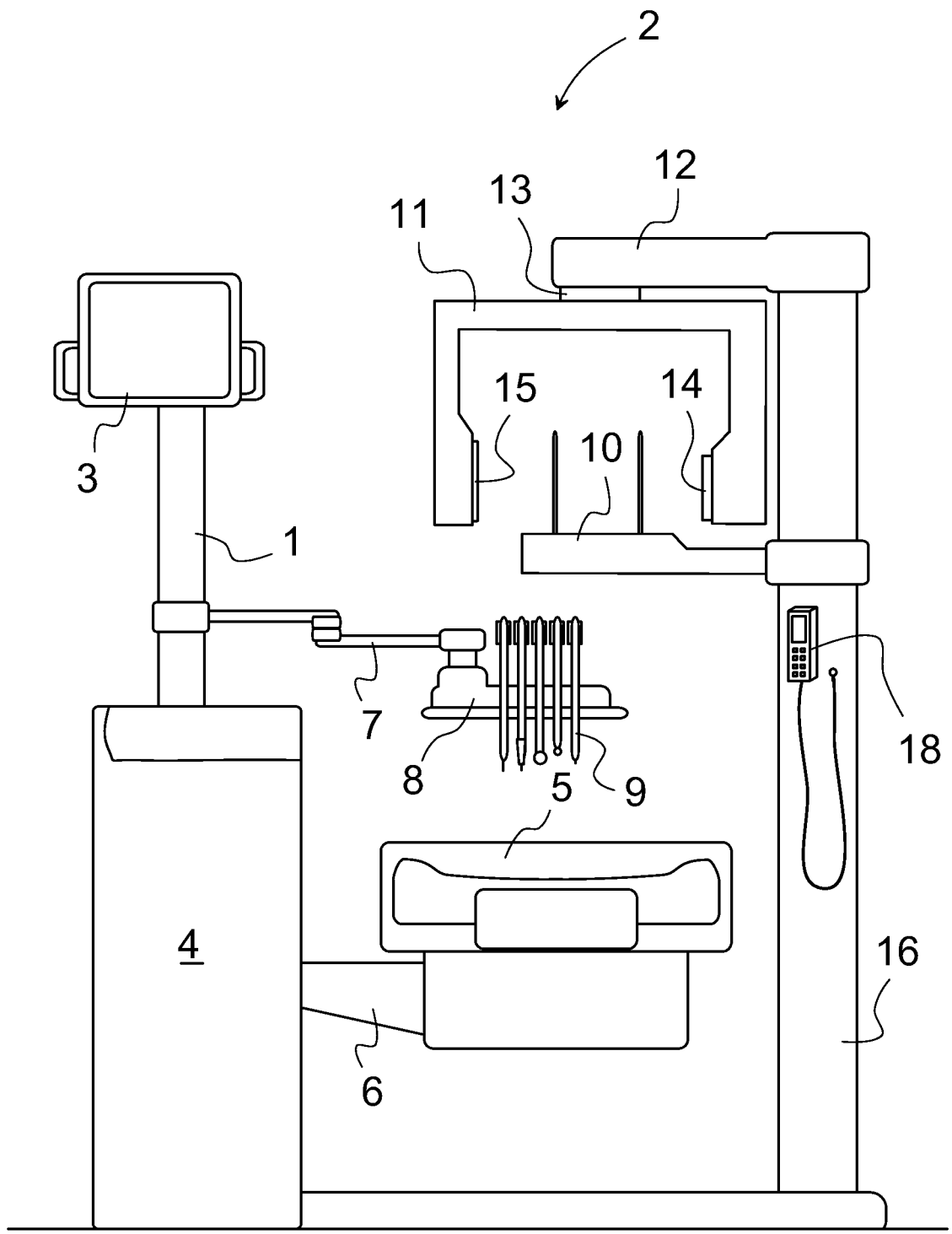
Figure 4:
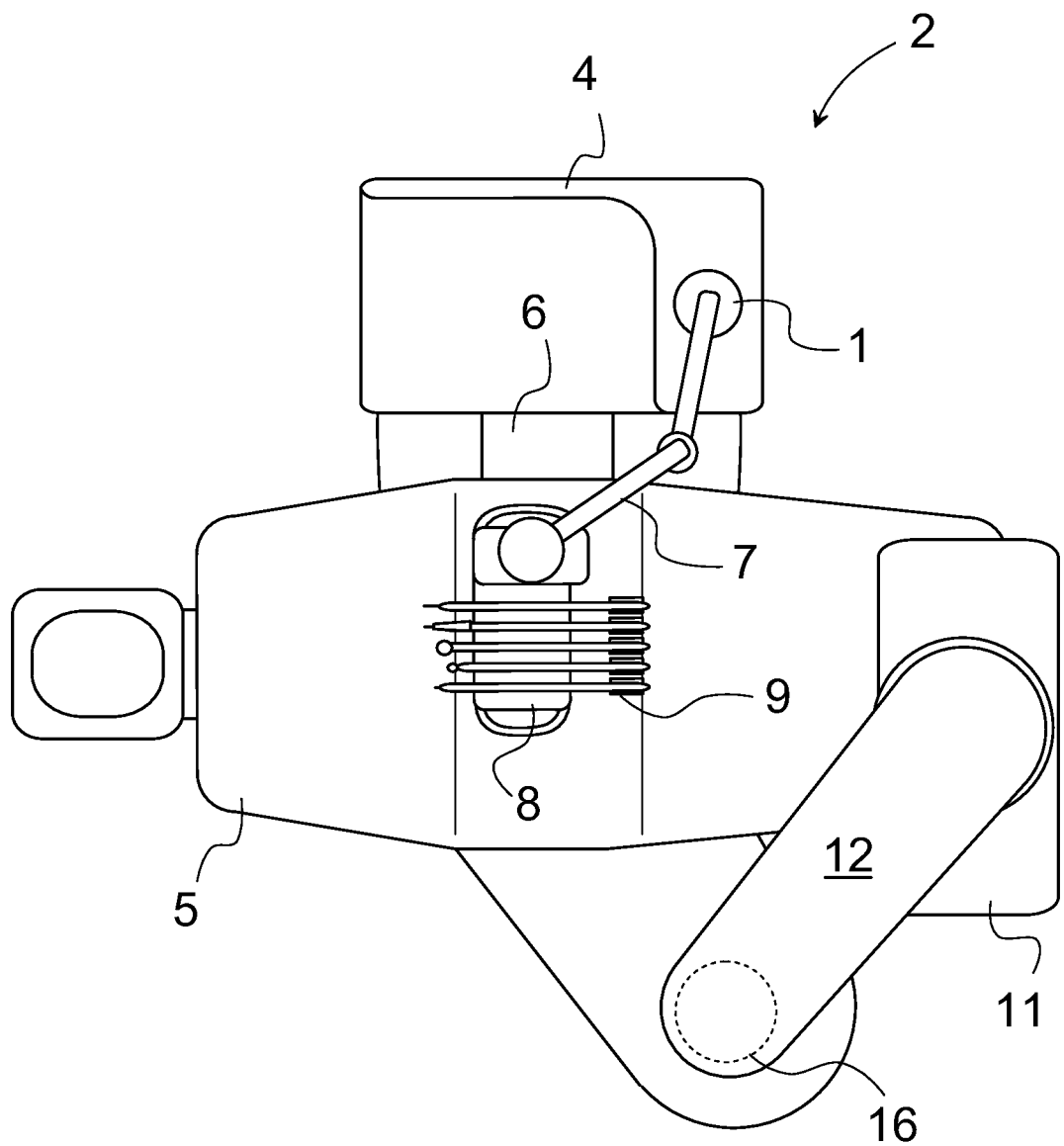
Figure 5:
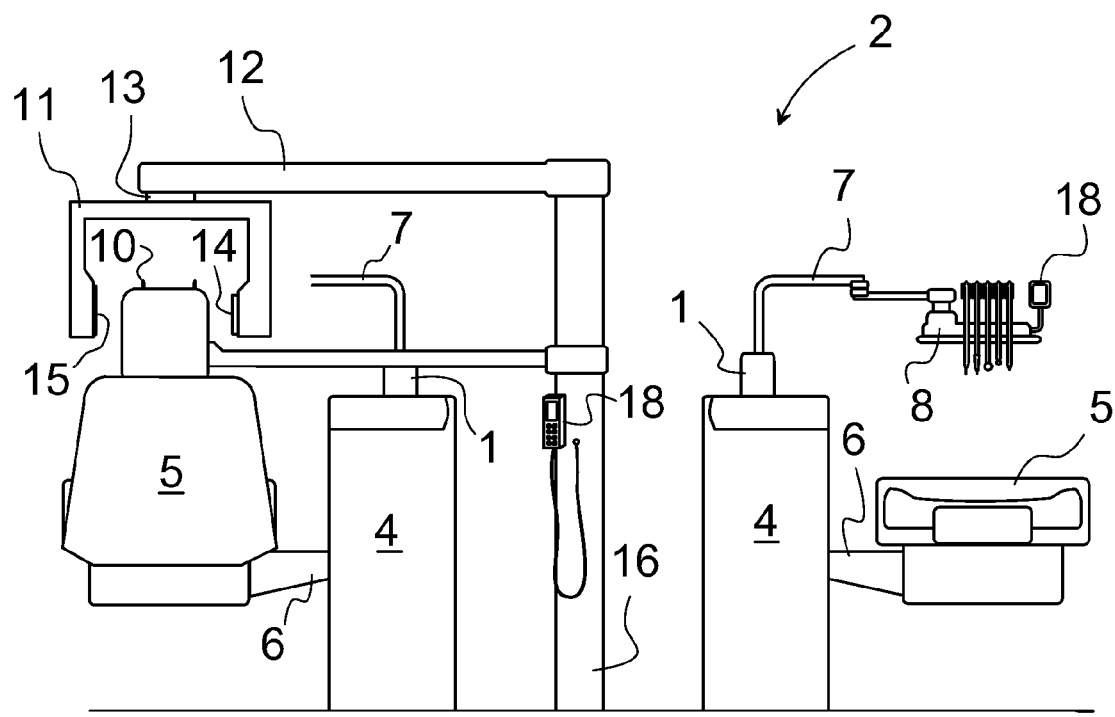
Figure 6:
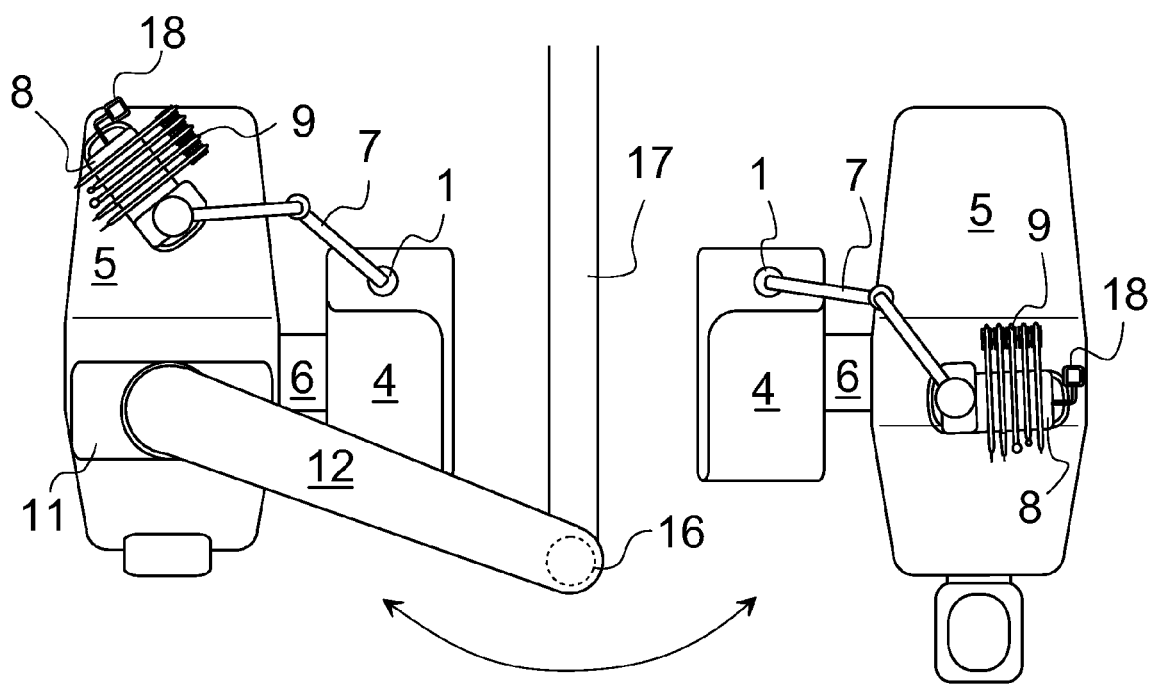

In the following, certain embodiments of the invention will be described in greater detail by also referring to the attached figures. The figures represent different embodiments of the invention in a simplified form and are not to be taken as dimensioned drawings. In the figures, FIG. 1 presents a side view of a first construction for an apparatus according to the invention, wherein an arm supporting imaging means is arranged in connection with a vertical arm provided in the dental care unit, FIG. 2 presents a top view of the construction according to FIG. 1, FIG. 3 presents a side view of a second construction for an apparatus according to the invention, wherein the arm supporting the imaging means is arranged in connection with a vertical arm disposed at a distance from the dental care unit, FIG. 4 presents the principle of the construction for an apparatus according to FIG. 3 in top view, FIG. 5 presents a side view of a solution for a dental treatment space according to the invention, wherein the apparatus according to the invention comprises two assemblies either consisting of a dental care unit and a patient chair, and one arm system supporting the imaging means, these structures being disposed substantially in conjunction with each other, and FIG. 6 presents the solution according to FIG. 5 as seen from above.

Figure 2:
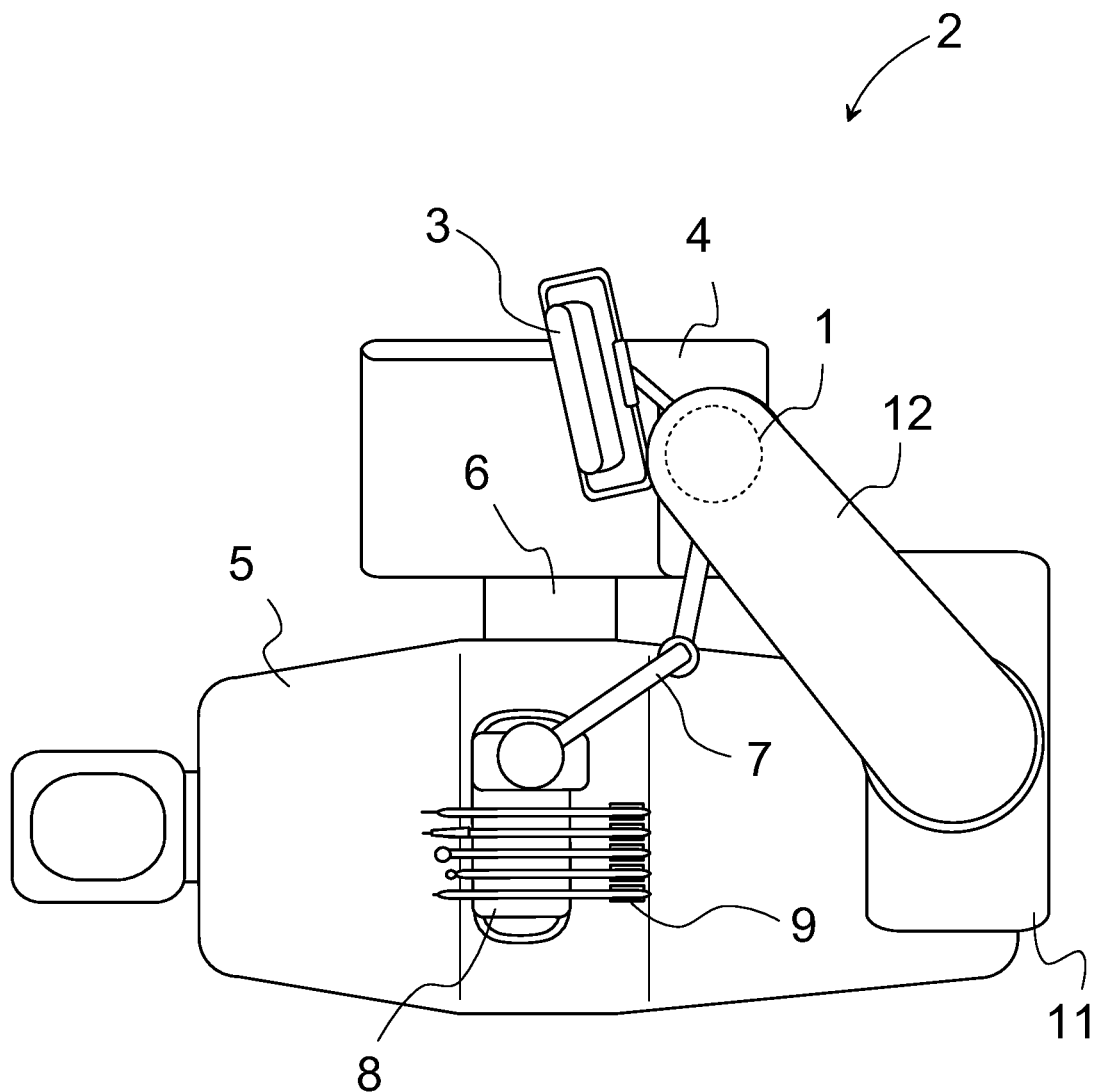

FIGS. 1 and 2 present the basic structure of one dental care apparatus 2 according to the invention as seen from the side and from above. The dental care apparatus 2 of FIGS. 1 and 2 comprises a dental care unit 4 designed for use in connection with dental care operations and a patient chair 5 arranged to be supported by an arm part 6 extending substantially horizontally from the dental care unit 4. A support column 1 extending substantially vertically from the dental care unit 4 has been arranged to support by means of a horizontally extending arm part 12 a substantially horizontally extending arm part 11 designed to carry imaging means (an X-ray source 14 and an image information receiver 15). Further, a patient support means 10, for positioning the patient substantially stationary for the imaging operation, is connected to the supporting column 1, as well as a display 3 and a treatment arm 7, which supports an instrument table 8 and the instruments 9 arranged thereto. The substantially vertically extending support column 1 can also be arranged to support other arms and accessories, such as e.g. an arm for a light.

The mounting of the arm part 11 carrying the imaging means 14, 15 is arranged to enable moving of the arm part 11.

Preferably, the arm part 11 is arranged to be at least turnable with respect to a substantially vertical axis 13 by means of at least one actuator, not shown in the figures. This vertical axis 13 has been arranged to be located, in the figures presented in this connection, in the area between the imaging means 14, 15, but it may be located elsewhere as well. This construction enabling rotating the arm part 11 may be a physical axle, but it may also be some other construction that enables a corresponding movement. Besides being arranged to be turnable, the arm part 11 carrying the imaging means 14, 15 is preferably also arranged movable, preferably by means of an actuator or actuators, so as location of the aforesaid vertical axis 13 in a horizontal plane can be changed. On the other hand, it is also possible to provide only a freedom of linear movement for the aforesaid arm part 11. The mounting of the substantially horizontally extending arm part 12 to the support column 1, which arm part 12 supports the arm part 11 carrying the imaging means 14, 15, may be arranged as turnable. The arm part 12 can also be arranged to consist of two or more arm parts turnable relative to each other. For the taking of X-ray images, the arm part 11 carrying the imaging means 14, 15 is arranged to be positioned or to be positionable at a suitable point above the patient chair 5, substantially at the point of the patient's head when the patient is in a sitting position. Correspondingly, the patient support means 10 is arranged to be positionable substantially at the point of the head of a patient in a sitting position.

In the embodiment represented by FIG. 1, the patient chair 5 has been arranged to be adjustable to different heights such that the patient chair 5 is supported by an arm part 6 extending from the dental care unit 4, while the means for raising and lowering the patient chair 5 have been arranged in the dental care unit 4. However, the patient chair 5 can also be arranged to be raised and lowered by a different construction, and it can even be implemented as a structure that is physically completely separate from the dental care unit 4 and/or separated from the latter at least in respect of externally visible parts and be provided with a elevating device construction of completely of its own. In this case, supporting of the patient chair 5 and changing of its height position can be implemented e.g. by a lever-arm type construction directly from the floor.

The treatment arm 7 may be an arm having two or more arm sections and provided with one or more joints. Typically, the treatment arm 7 is arranged to be easily movable in different directions and, on the other hand, to hold the instrument table 8 steady at its set position. The physical quantities required for operation of the instruments 9 are received from the dental care unit 4, which is arranged to take care of controlling the instruments 9 and of supplying them with operating power, such as electricity and compressed air, via hoses, cables or equivalent arranged inside the treatment arm 7.

According to one preferred embodiment of the invention, the resources needed by the imaging means 14, 15 and the means for moving them, as well as the associated connections, can be disposed in connection with the dental care unit 4, even so as to be at least partly shared by the corresponding means of the dental care unit 4 and/or the patient chair 5. The display 3 comprised in the apparatus 2 may be arranged to function as a user interface as well, and it can be arranged to control, besides controlling the functions of the dental care unit 4 and the patient chair 5, the operation of the X-ray source 14 and the imaging sensor 15 and/or of the actuator or actuators moving these. On the other hand, the display 3 may function as a means of displaying data relating to the dental treatment, the patient and the dental instruments, but also as a means for displaying e.g. the images taken by the imaging means of the apparatus.

FIGS. 3 and 4 present the basic construction of a second dental care apparatus 2 according to the invention in lateral and top views. For the sake of clarity, the FIG. 4 presenting the apparatus 2 in top view has been slightly simplified by omitting some of the parts of the apparatus 2 shown in FIG. 3.

In the embodiment according to FIG. 3, the apparatus comprises a substantially vertical support column 1 arranged in connection with the dental care unit 4, but now the arm part 11 carrying the imaging means 14, 15 is not arranged to be connected to this support column 1 but to a vertically extending support column 16 arranged at a distance from the dental care unit 4. In the embodiment according to FIGS. 3 and 4, the support column 16 in question is so disposed that the patient chair 5 is positioned between this supporting column 16 and the dental care unit 4. The support column 16, the arm parts 11, 12 carrying the imaging means 14, 15 and the patient support means 10 are so disposed relative to the patient chair 5 that they will not hinder the dentist's normal treatment work at the head rest end of the patient chair 5. In the embodiment according to FIGS. 3 and 4, the support column 16 and the dental care unit 4 are placed on a common base structure, which arrangement may facilitate the provision of shared resources for the imaging means 14, 15 and the dental care unit 4. In principle, though, the dental care unit 4 and the support column 16 can also be implemented using independent support and connection structures. Besides, the support column 16 need not necessarily be mounted on the floor as the essential point is that the construction allows positioning of the imaging means 14, 15 relative to the patient chair 5 in a manner according to the invention.

In the solution according to FIG. 3, the patient support means 10 designed to be positioned above the patient chair 5 is arranged on the same support column 16 with the imaging means 14, 15, but it can also be arranged to be attached e.g. to the support column 1 extending vertically from the dental care unit 4 or to some other suitable structure, for example to the patient chair itself.

In the embodiment according to FIG. 3, a user interface 18 has been arranged on the supporting column 16. This user interface may be arranged to be used for the control of the imaging means 14, 15 and of the actuator or actuators of the arm part 11 or arm parts carrying them, but additionally or alternatively for the control of the dental instruments 9 used for dental care operations and/or of the patient chair 5. The user interface 18 can be arranged to transmit signals to and/or from at least one of the following: the actuator or actuators of the arm part 11 or arm parts carrying the imaging means 14, 15, the radiation source 14, the image information receiver 15.

More generally speaking, the apparatus 2 of the invention need not necessarily be provided with separate user interfaces 18 for different purposes, but the control of the apparatus can be arranged to be effected from a single user interface 18. Such a user interface 18 can be arranged e.g. in connection with the instrument table 8 of the dental care unit 4 as illustrated in FIGS. 5 and 6.

FIGS. 5 and 6 represent an embodiment of the invention which comprises the same basic solutions as those described above, except that the apparatus 2 now has two assemblies comprising a dental care unit 4 and a patient chair 5, and one arm system 11, 12 as described above for carrying the imaging means 14, 15 and the patient support means 10, arranged in functional connection with each other. In this embodiment of the invention, the support column 16 of the arm system 11, 12 supporting the imaging means 14, 15 is arranged to form a part of a wall or a panel 17 provided between the aforesaid assemblies consisting of a dental care unit 4 and a patient chair 5. As a whole, the arm system 11, 12 carrying the imaging means 14, 15 is so implemented that both the arm part 11 carrying the imaging means 14, 15 and the patient support means 10 are arranged to be positionable substantially above each patient chair 5. In the solution according to FIGS. 5 and 6, each patient chair 5 is supported by a support arm 6 extending from the dental care unit 4. In such a solution, the means for adjusting the height position of the patient chair 5 can be provided in the dental care unit 4 as described above.

For the sake of clarity, some of the structures presented in FIG. 6 are not presented in FIG. 5, and vice versa. Thus, for example, FIG. 5 shows the user interface 18 arranged on the support column 16, whereas FIG. 6 shows only the user interfaces 18 arranged in conjunction with the instrument table 8 of the dental care units 4. As stated above, generally speaking the apparatus 2 according to the invention may be realized as comprising a single user interface only, i.e. there is no need to necessarily arrange separate user interfaces 18 for e.g. the dental care unit 4 and the imaging means 14, 15 (and for the actuators moving the arm part or arm parts supporting them).

The apparatus may also comprise more than two, e.g. four assemblies consisting of a dental care unit 4 and a patient chair 5, in which case the arm part 11 carrying the imaging means 14, 15, which has been arranged movable, is arranged to be positionable above each patient chair 5. Considering FIGS. 5 and 6, the patient support means 10 and the arm system 11, 12 carrying the imaging means 14, 15 attached to the support column 16 would in this case be turnable to a position above each one of the four patient chairs 5, arranged e.g. in two rows with the head rest ends opposite to each other, so as to allow for an x-ray image to be taken of a patient in a sitting position on a patient chair 5.

In more general terms, this type of embodiment of the invention thus comprises at least two assemblies consisting of a dental care unit 4 and a patient chair 5 arranged in substantial vicinity of each other and one support column 16, to which are connected at least one substantially horizontally extending arm part 11 arranged to be moved by an actuator and, arranged on this arm part 11 at a distance from each other, an X-ray source 14 and an image information receiver 15, said arm part 11 being arranged to be positionable substantially above at least these two patient chairs 5.

Generally speaking, the various embodiments of the present invention comprise a dental care apparatus 2 which comprises a dental care unit 4 and a patient chair 5 arranged in the immediate vicinity of each other and to which apparatus 2 is structurally connected at least one of the following: a treatment arm 7 for dental care instruments 9, an arm for holding some other appliance or device used in a dental environment, such as a display 3, and which dental care apparatus 2 comprises at least one arm part 11 arranged at least physically in the immediate vicinity of the dental care unit 4 and arranged to be moved by an actuator and, arranged on this arm part 11 at a distance from each other, an X-ray source 14 and an image information receiver 15, in which apparatus 2 said arm part 11, arranged to carry the imaging means 14, 15, and the patient chair 5 are so disposed relative to each other that the arm part 11 lies or is positionable substantially above said patient chair 5.

In certain preferred embodiments of the invention, the dental care apparatus 2 is provided with a user interface 18 which is arranged to transmit control commands both to the dental care unit 4 and/or the patient chair 5 and to at least one of the following: an actuator for an arm part 11 arranged to be movable, a radiation source 14, an image information receiver 15. The apparatus 2 may further comprise a control system comprising control routines and control means for controlling, on the one hand, an actuator or actuators for an arm part 11 carrying imaging means 14, 15, a radiation source 14 and an image information receiver 15 and, on the other hand, at least the dental care unit 4, said aforementioned control system of the apparatus 2 being arranged partially or completely as part of another control system for the dental care unit 4.

The various embodiments of the invention allow for at least some of the means for e.g. transmitting electric power and/or information to or from at least one of the following: actuator for an arm part 11 arranged to be rotatable, a radiation source 14, an image information receiver 15, to be integrated or arranged in functional connection with the corresponding means of the dental care unit 4.

As the said radiation source 14 and image information receiver 15 as well as the arm part 11 arranged to be movable and carrying them have been arranged to position or be positionable so that said arm part 11 positions substantially above the skull of a patient in a sitting position and the said radiation source 14 and image information receiver 15 substantially on opposite sides of the skull, the patient can be exposed without a need for the patient to leave the patient chair 5 to be imaged. The head rest of the patient chair 5 can be so implemented that it will not hinder a possible rotational or other motion of the imaging means 14, 15 on different sides of the patient's head. The patient can also be imaged in a sitting position without having the back rest of the patient chair 5 being raised to a sitting position during exposure.

The apparatus 2 can be provided with means for adjusting the height position of the movably arranged arm part 11 (which carries the imaging means 14, 15). The height adjustment can be implemented e.g. by providing the support column 1, 16 with means for varying its length, by means of which the height position of the imaging arm system 11, 12 as a whole can be adjusted individually for each patient. The patient support means 10 can be arranged to move along with this adjusting movement. In a preferred embodiment of the apparatus, however, the column and arm system 1, 16, 11, 12 supporting the imaging means is implemented as relatively light by omitting such elevator construction from it altogether, and the adjustment of the height position for individual patients is realized by using means provided in the apparatus 2 for adjusting the height position of the patient chair 5.

The aforesaid display 3 arranged on the support column 1, 16 can be arranged to be in functional connection with at least, on the one hand, the aforesaid dental care unit 4 and, on the other hand, the aforesaid means for receiving image formation 14. The apparatus can also be provided with more than one display 3.

The apparatus 2 can be arranged to allow X-ray imaging e.g. by providing it with a such control system that, when one movably mounted arm part 11 comprising the imaging means 14, 15 has been so positioned that the arm part 11 is positioned substantially above the skull of a patient in a sitting position, and when said arm part 11 has been arranged to be both rotatable about a substantially vertical axis 13 and movable in a substantially horizontal plane so as to allow the position of the aforesaid vertical rotation axis 13 in the horizontal plane to be changed it is possible, under control of the control system, both to produce a given movement of the imaging means 14, 15 relative to the patient's skull positioned on the patient support means 10 and, while said movements are being carried out, to have X-radiation produced by the radiation source 14—and, depending on the imaging method, when required also to control the image information receiving means 15. This kind of an arrangement allows versatile imaging, such as panoramic X-ray imaging which is typical in connection with dental X-ray imaging. In different embodiments of the invention, the motion of the arm part 11 supporting the imaging means 14, 15 can be implemented using simple constructions to permit e.g. only a turning movement or a linear movement of the arm part 11, and, on the other hand, at its most versatile, using constructions that allow free positioning and motion of the arm part 11 within the operation range the construction makes possible.

In different embodiments of the invention, the apparatus 2 is provided with means for transmitting electric power and/or information to or from at least one of the following: actuator of the arm part 11 arranged to be rotatable, radiation source 14, image information receiver 15; such that at least some of these means have been arranged as integrated with corresponding means of the dental care unit 4 and/or the patient chair 5. The radiation source 14, the image information receiving means 15 and the arm part 11 carrying them are arranged to be positioned such that the arm part 11 positions substantially above the skull of the patient sitting on the patient chair 5 and said radiation source 15 and image information receiving means 16 substantially on opposite sides of the skull. The apparatus is thus preferably also provided with means for adjusting the relative height position of the patient chair 5 and/or that of the aforesaid arm part 11 arranged to be rotatable, such as the support arm 6 for adjusting the height position of the patient chair 5.

Regarding supporting the imaging means 14, 15, the apparatus comprises a preferably substantially vertical support column 1 or a corresponding structure 1, 16, and the arm part 11 carrying the imaging means 14, 15 is attached to this support column 1, 16 via at least one other arm part 12 extending substantially horizontally. A support column 1, 16 like this can be disposed on the dental care unit 4 or in substantial vicinity of the dental care unit 4, e.g. immediately on the other side of the patient chair 5, or it can even be arranged to be attached to the patient chair 5. The patient support means 10 is arranged to be positioned or positionable substantially above the patient chair 5, between the aforesaid X-radiation source 14 and image information receiver 15 being arranged at a distance from each other.

Further, the at least one arm part 11 carrying the imaging means 14, 15 and the radiation source 14 and the image information receiver 15 arranged on this arm part 11 at a distance from each other may be so arranged in the apparatus that this arm part 11 is positioned or positionable substantially above the skull of a patient in a sitting position, and the apparatus is preferably so implemented that this arm part 11 can be both turned relative to a substantially vertical axis 13 and moved in a substantially horizontal plane in a manner such that the position of this vertical rotation axis 13 in the horizontal plane 5 changes, and that the apparatus 2 comprises such a control system under control of which said arm part 11 can be turned and/or moved and X-radiation produced from the radiation source 14 simultaneously with said movement.

One preferable embodiment of the invention includes a construction in which the patient chair 5 has been arranged rotatable about a vertical axis. In this case, considering the construction of FIG. 1, it is not necessary to arrange in the apparatus an arm part 11 carrying both of the imaging means 14, 15, but one of the imaging means 14 or 15 can be arranged attached to e.g. the support arm 1 vertically extending from the dental care unit 4, or to some other applicable structure, and only the other of the imaging means 14 or 15 attached to the arm part 11. Thereby, one is able to realize the arm construction 11, 12 of the apparatus carrying at least the other of the imaging means 14, 15 as structurally lighter and simpler, as there is less mass to be supported. Further, in case the apparatus will be arranged to be used e.g. specifically for cranial CT imaging, the required changing of the mutual position of the patient and the imaging means can be realized without moving the imaging means 14, 15 by turning the patient chair 5. In this case, it is not necessary to arrange in the apparatus actuators or other means for turning the imaging means about the patient's skull.

It is obvious to a person skilled in the art that the invention is not limited to the embodiments described above. For example, let it be made clear here that in the apparatus of the invention, it is possible to use as an image information receiver i.a. a traditional film, a narrow digital sensor applicable for dental panoramic imaging or a wider one applicable for cone beam tomography.

The invention claimed is:

1. A dental care apparatus, which comprises:
   a dental care unit and a patient chair arranged in an immediate vicinity of the dental care unit, wherein the dental care unit supplies one or more physical magnitudes to one or more dental care instruments for the operation thereof, said physical magnitudes including at least one of electricity, compressed air, water and suction;
   at least one of a treatment arm for said one or more dental care instruments and an auxiliary arm for some other appliance or device used in a dental care environment said at least one of the treatment arm and the auxiliary arm being structurally connected to a part of the dental care apparatus other than said at least one of the treatment arm and the auxiliary arm themselves;
   at least one arm system arranged in an immediate vicinity of the dental care unit and carrying imaging means including an X-radiation source and an image information receiver, said imaging means being operative to perform dental extra-oral imaging,
   wherein a mutual position of said at least one arm system and said patient chair is arranged such that the at least one arm system is positioned or positionable substantially above the patient chair; and
   an actuator and a control system, wherein at least part of said at least one arm system carrying the imaging means, and/or the patient chair, is arranged rotatable by the actuator being controlled by the control system.

2. A dental care apparatus according to claim 1, wherein said at least one arm system includes an arm part arranged to be rotatable by the actuator and to carry said X-radiation source and said image information receiver at a distance from each other on opposite sides of a patient's skull.

3. A dental care apparatus according to claim 2, wherein the arm part carrying the imaging means is so arranged in the apparatus that said arm part
   positions or is positionable substantially above a skull of a patient in a sitting position and
   can be turned relative to a substantially vertical axis and moved in a substantially horizontal plane in a manner such that position of a vertical rotation axis of said arm part in the horizontal plane changes, and
   wherein said control system of the apparatus is arranged to enable turning and/or moving said arm part and, simultaneously with said movement, production of X-radiation by the X-radiation source.

4. A dental care apparatus according to claim 1, wherein the patient chair is arranged rotatable by the actuator.

5. A dental care apparatus according to claim 1, further comprising a user interface arranged to transmit control commands to the dental care unit and/or to the patient chair and further to at least one of the following: the actuator, the X-radiation source, and the image information receiver.

6. A dental care apparatus according to claim 1, wherein said control system comprises control routines and control means for controlling said actuator, said X-radiation source, said image information receiver and said dental care unit.

7. A dental care apparatus according to claim 1, further comprising means for transmitting electric power and/or information to or from at least one of the following: the actuator, the X-radiation source, the image information receiver, and wherein at least some of the means for transmitting electric power and/or information are arranged to be integrated with and/or functionally connected to corresponding means for transmitting electric power and/or information arranged to the dental care unit and/or the patient chair.

8. A dental care apparatus according to claim 1, wherein said X-radiation source and said image information receiver as well as said at least one arm system carrying the imaging means are arranged to be positioned such that said at least one arm system positions substantially above a skull of a patient in a sitting position in the patient chair, and said X-radiation source and the image information receiver substantially on opposite sides of the skull.

9. A dental care apparatus according to claim 1, further comprising a means for adjusting a relative height position of the patient chair and the at least one arm system.

10. A dental care apparatus according to claim 9, wherein said means for adjusting a relative height position of the patient chair and the at least one arm system is arranged in connection with the dental care unit and include means for adjusting a height position of the patient chair.

11. A dental care apparatus according to claim 1, further comprising a substantially vertical support structure for supporting said at least one arm system arranged to carry the imaging means, wherein said at least one arm system includes a substantially horizontally extending arm part and wherein said at least one arm system is attached to said support structure via said arm part extending substantially horizontally.

12. A dental care apparatus according to claim 1, further comprising a substantially vertical support structure arranged to the dental care unit and wherein said treatment arm arranged for dental instruments and said at least one arm system carrying the imaging means are attached to said substantially vertical support structure.

13. A dental care apparatus according to claim 1, further comprising a substantially vertical support structure arranged in substantial vicinity of the dental care unit and wherein said treatment arm arranged for dental instruments and said at least one arm system carrying the imaging means are attached to said substantially vertical support structure.

14. A dental care apparatus according to claim 1, wherein said X-radiation source and said image information receiver are arranged at a distance from each other and said dental care apparatus further includes a patient support means positioned or arranged to be positionable substantially above the patient chair, between said X-radiation source and said image information receiver arranged at a distance from each other.

15. A dental care apparatus comprising:
   a first assembly including:
      a first dental care unit, and
      a first patient chair arranged in a substantial vicinity of the first dental care unit;
   a second assembly including:
      a second dental care unit, and
      a second patient chair arranged in a substantial vicinity of the second dental care unit;
   a support;
   an imaging means including an X-radiation source and an image information receiver, said imaging means being operative to perform dental extra-oral imaging; and
   at least one arm system including an actuator supported by and extending from said support, said at least one arm system arranged to be moved by the actuator, said at least one arm system supporting the imaging means, and said at least one arm system being arranged to selectively position the imaging means substantially above both of said first patient chair and said second patient chair;
   wherein each of the first dental care unit and the second dental care unit includes, structurally connected thereto, at least one of: (i) a treatment arm for carrying dental care instruments and (ii) an arm for supporting at least one other device used in a dental care environment.

16. A dental care apparatus according to claim 15, further comprising means for adjusting a height position of each of the first and second patient chairs.

17. A dental care apparatus according to claim 15, further comprising:
   a third assembly including a third patient chair and a third dental care unit and a fourth assembly including a fourth patient chair and a fourth dental care unit, wherein said at least one arm system is arranged to be movable so as to selectively position the imaging means substantially above the first, the second, the third and the fourth patient chairs.

* * * * *